United States Patent
Nicolas et al.

(10) Patent No.: US 6,643,536 B2
(45) Date of Patent: Nov. 4, 2003

(54) SYSTEM AND METHOD FOR SYNCHRONIZATION OF THE ACQUISITION OF IMAGES WITH THE CARDIAC CYCLE FOR DUAL ENERGY IMAGING

(75) Inventors: Francois Serge Nicolas, Wauwatosa, WI (US); Amber Elaine Rader, Brookfield, WI (US); Michael John Barber, Mequon, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 349 days.

(21) Appl. No.: 09/752,283

(22) Filed: Dec. 29, 2000

(65) Prior Publication Data

US 2002/0087074 A1 Jul. 4, 2002

(51) Int. Cl.⁷ .................................................. A61B 5/05
(52) U.S. Cl. ..................................................... 600/428
(58) Field of Search ............................... 600/428, 429, 600/407, 425, 413, 417; 378/21

(56) References Cited

U.S. PATENT DOCUMENTS

| | | | | |
|---|---|---|---|---|
| 4,289,142 A | * | 9/1981 | Kearns | 600/529 |
| 4,382,184 A | * | 5/1983 | Wernikoff | 378/37 |
| 4,433,428 A | * | 2/1984 | Haendle et al. | 378/95 |
| 4,611,340 A | * | 9/1986 | Okazaki | 378/95 |
| 4,662,379 A | * | 5/1987 | Macovski | 600/428 |
| 5,084,912 A | * | 1/1992 | Barr | 378/98.2 |
| 5,308,310 A | * | 5/1994 | Roff et al. | 600/21 |
| 5,668,844 A | * | 9/1997 | Webber | 378/2 |
| 5,832,051 A | * | 11/1998 | Lutz | 378/8 |
| 6,413,223 B1 | * | 7/2002 | Yang et al. | 600/485 |
| 6,501,979 B1 | * | 12/2002 | Manning et al. | 600/413 |
| 6,507,639 B1 | * | 1/2003 | Popescu | 378/10.8 |
| 6,510,337 B1 | * | 1/2003 | Heuscher et al. | 600/428 |

* cited by examiner

Primary Examiner—Daniel Robinson
(74) Attorney, Agent, or Firm—McAndrews, Held & Malloy, Ltd.; Peter J. Vogel; Michael A. Dellapenna (57) ABSTRACT

A system and method for improving the image quality of an X-ray image of a patient in a dual energy X-ray imaging system is provided. The system includes a heart cycle monitor, and X-ray emitter and an X-ray detector. A patient is positioned between the X-ray emitter and the X-ray detector. The heart cycle monitor monitors the cardiac cycle of the patient to detect a cardiac trigger. Once the cardiac trigger has been detected, the X-ray emitter emits high energy and low energy X-rays through the patient and the X-ray detector detects the emissions and forms images. The X-ray detector then performs a number of scrubs. Then the X-ray emitter acquires at least one offset image. The offset and the X-ray images are then combined to form X-ray images that may then be employed for dual energy X-ray processing.

38 Claims, 3 Drawing Sheets

SYSTEM AND METHOD FOR SYNCHRONIZATION OF THE ACQUISITION OF IMAGES WITH THE CARDIAC CYCLE FOR DUAL ENERGY IMAGING

BACKGROUND OF THE INVENTION

The preferred embodiments of the present invention generally relate to improvements in a medical X-Ray imaging system. More particularly, the present invention relates to a system and method for synchronizing the acquisition of images with the cardiac phase for dual energy imaging.

The usage of X-ray systems in clinical imaging and diagnosis enjoys widespread acceptance. Several types of X-ray imaging methodologies may be employed to image different anatomical areas or to provide differing diagnostic tools. One such X-ray imaging methodology is Dual Energy (DE) imaging.

Dual Energy (DE) is a clinical application wherein two x-ray images are acquired at different X-ray energies. The two X-ray images are then combined to provide tissue-subtracted images, e.g., soft tissue and bone images. One clinical application of DE is diagnosis of lung cancer with X-ray. In practice, the soft tissue image improves sensitivity by removing the structured noise due to the bones, and the bone image improves specificity by showing if a nodule is calcified and hence benign.

With flat panel X-ray detector technology, the two X-ray images are typically successively acquired with two separate X-ray exposures at different energies. In order to minimize patient motion artifacts between the two X-ray images, the time between the X-ray images is typically minimized (typically on the order of 200 ms). In order to minimize diaphragm motion, the patient is typically asked to hold their breath. However, involuntary patient motion such as the contraction of the heart, cannot be avoided. Significant motion of the heart between the two X-ray images may yield poor image quality due to imperfect tissue cancellation in the subtracted images. The poor image quality may lead to possible missed cancer nodules in the lung regions surrounding the heart.

Thus, a need has long been felt for a system that provides for better diagnostic X-ray imaging. Specifically, a need has long been felt for an improved diagnostic X-ray imaging system for employing DE. Further, a need has long been felt for such an improved DE system that minimizes the effect of involuntary patient motion in the resultant X-ray images in order to improve image quality and consequent diagnosis.

BRIEF SUMMARY OF THE INVENTION

The present invention provides a system and method for improving the image quality of an X-ray image of a patient in a dual energy X-ray imaging system. The X-ray emitter emits high and low energy X-rays which may be combined with offsets. Both the high and low energy X-rays are triggered by a heart cycle monitor which determines the patient's cardiac events. An X-ray detector receives the X-ray emissions and offsets and forms X-ray images. The heart monitor is employed to synchronize the X-ray imaging of the patient with the patient's cardiac cycle in order to minimize the effect of involuntary patient motion and improve the resultant X-ray images.

DETAILED DESCRIPTION OF THE INVENTION

Figure 1:
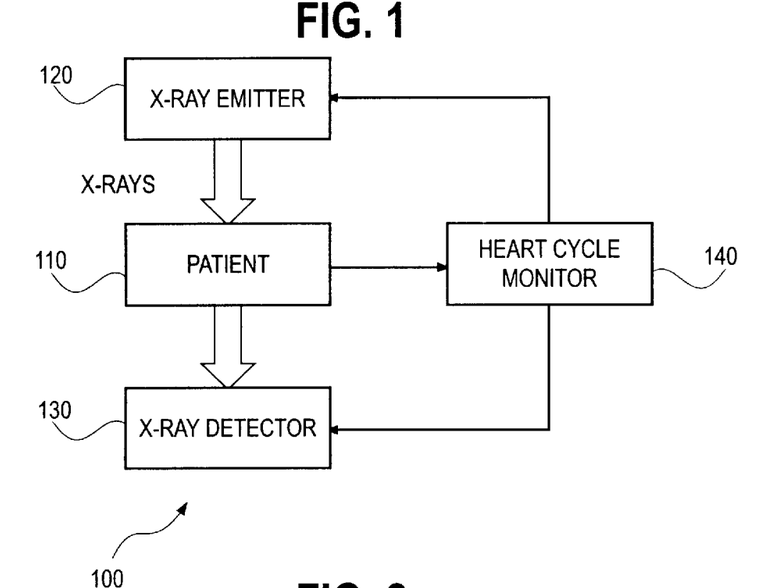
FIG. 1 illustrates an image acquisition synchronization system according to a preferred embodiment of the present invention.

FIG. 1 illustrates an image acquisition synchronization system 100 according to a preferred embodiment of the present invention. The synchronization system 100 includes a patient 110, an X-ray emitter 120, an X-ray detector 130, and a heart cycle monitor 140. The heart cycle monitor 140 tracks the heart cycle of the patient 110 and controls the X-ray emitter 120 and X-ray detector 130.

In operation, the patient 110 is placed between the X-ray emitter 120 and the X-ray detector 130 of an X-ray imaging system. The heart cycle monitor 140 then monitors the patient's heart cycle. The heart cycle monitor 140 signal is used to control the X-ray emitter 120 and X-ray detector 130 to synchronize X-ray acquisition with the patient's 110 cardiac cycle.

The preferred embodiment of the present invention provides a system and method to synchronize the acquisition of two images of the patient's 110 chest with the patient's heart cycle. By synchronizing the images, the synchronization system 100 reduces the likelihood of artifacts due to heart motion in the X-ray image. Preferably, the acquisition of the two images occurs during the diastolic portion of the cardiac cycle. Diastole is the portion of the cycle when the heart is filling rather than contracting, producing minimal movement of the heart.

The heart cycle monitor 140 may be any of a variety of heart cycle monitoring devices. Preferably, the heart cycle monitor 140 is a finger pulse plethysmograph or a wall stand integrated plethysmograph. The finger pulse plethysmograph is a device that attached to the patient's 110 finger and measures the patient's 110 blood pressure. The patient's blood pressure varies during the heart cycle. Thus, by measuring the variations in the patient's blood pressure, the plethysmograph may be used to determine the patient's 110 cardiac cycle. The wall stand integrated plethysmograph includes pulse plethysmograph directly integrated into an X-ray wall stand. Preferably, the patient is positioned and the patient then holds the pulse plethysmograph. The wall stand integrated plethysmograph may also assist the patient in holding their arms away from their body, as preferred during the X-ray imaging procedure. The use of the wall stand integrated plethysmograph thus reduces the burden on the technician of having to attach the plethysmograph to the patient. Typically, a delay occurs between heart contraction and the receipt of the plethysmograph signal. The delay is typically approximately 150 ms.

FIGS. 2–5 illustrate four different embodiments of the image acquisition synchronization system 100 of FIG. 1.

FIGS. 2–5 are not to scale with respect to the heart cycle or the timing of the sequence events with respect to the rendition of the heart cycle. Each of the embodiments of FIGS. 2–5 synchronizes the acquisition of the two X-ray images between the detector cycle and the heart cycle. The embodiments of FIGS. 2–5 select among the following variables: 1) fixed or variable frame time, 2) immediate, preplanned image acquisition based on monitored heart rate or image acquisition on next read, and 3) both high and low kVp exposures in the same heart cycle or in successive heart cycles.

First, with regard to the selection of fixed or variable frame time, the frame time is the time between two successive detector readouts. The frame time is a parameter of the imaging system while the exposure time may vary depending upon the X-ray dosage. For example, for high kVp X-rays, the exposure time may be lower. Unfortunately, many commercially available X-ray systems do not offer variable frame time options. Thus, the frame time may be a fixed system parameter in some cases. Having a fixed frame time may simplify the implementation of the medical imaging system because the system only requires a single offset image for use with both high and low kVp images. However, using a variable frame time corresponding to the actual exposure time of the high and low kVp images may yield a more accurate image as discussed below.

Second, with regard to immediate, preplanned image acquisition based on monitored heart rate or image acquisition on next read, acquisition of the X-ray image from the X-ray detector 130 is accomplished by performing a "read" from the X-ray detector 130. Once a read has begun, the read may not be interrupted. Consequently, there are two options. First, when the cardiac trigger has been received from the heart cycle monitor 140, the system 100 may complete its current read (frame cycle), then transmit X-rays, and then read from the X-ray detector 130. Alternatively, the heart cycle monitor 140 may monitor the heart cycle to predict when the cardiac trigger is to occur and then schedule the X-ray transmission to occur immediately thereafter (without waiting for the end of the frame cycle), followed by a read of the detector 130.

Third, with regard to both high and low kVp exposures in the same heart cycle or in successive heart cycles, the system 100 may trigger both the low (or high) kVp emission and the high (or low) kVp emission successively during the same heart cycle. Alternatively, the system 100 may trigger one emission and an offset in the same heart cycle and then one emission of the other kVp (high or low) followed by an offset in the next successive heart cycle. For example, the system 100 may trigger the high kVp emission in the first heart cycle and may trigger the low kVp emission in the second heart cycle.

Figure 2:
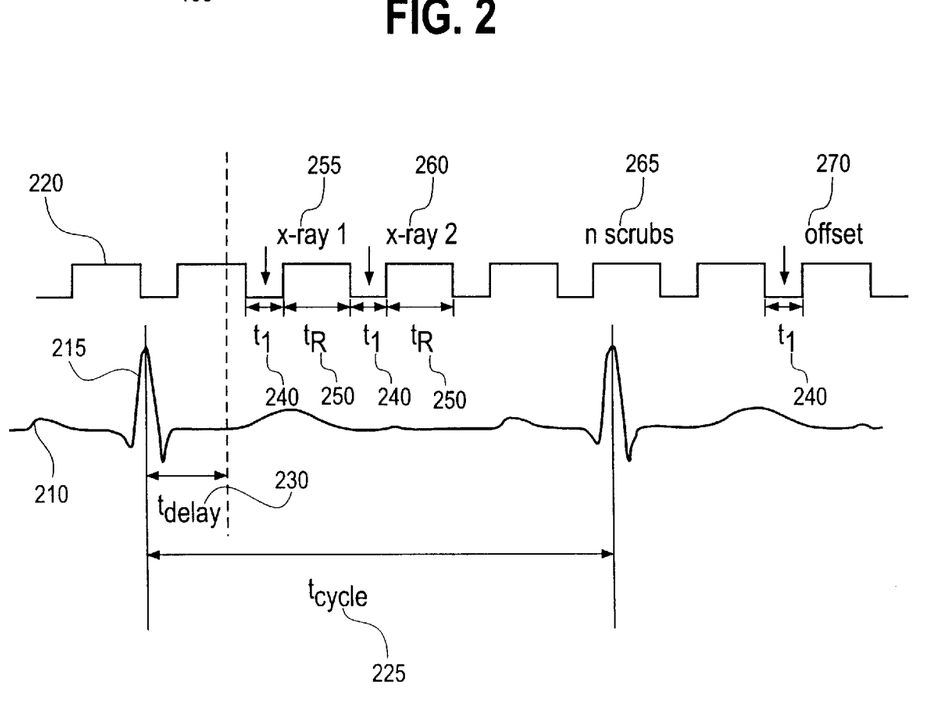
FIG. 2 illustrates the synchronization system as applied with fixed frame time, acquisition on next read, and both kVp exposures in the same heart cycle according to a preferred embodiment of the present invention.

FIG. 2 illustrates the synchronization system 100 as applied with fixed frame time, acquisition on next read (based on the example heart cycle phase), and both exposures in the same heart cycle according to a preferred embodiment of the present invention. FIG. 2 includes a heart cycle trace 210, a cardiac trigger 215, a detector read trace 220, cycle time ($t_{cycle}$) 225, delay time ($t_{delay}$) 230, frame time ($t_1$) 240, detector readout time ($t_R$) 250, a first fixed-time kVp X-ray exposure 255, a second fixed-time kVp X-ray exposure 260, scrubs 265, and an offset 270.

The cycle time 225 is the average cardiac cycle time of approximately 900 ms. The delay time 230 is the typical delay between the actual contraction of the heart and the receipt of the contraction signal at the heart cycle monitor 140, for example a plethysmograph. The delay time is typically approximately 150 ms. The exposure time 240 is the length of time that the X-ray emitter 120 emits X-rays. In the embodiment of FIG. 2, the frame time 240 is fixed. Because the exposure time for the lower kVp emission is typically longer than the exposure time for the higher kVp exposure, the frame time 240 is fixed at the exposure time for the lower kVp exposure. The detector readout time 250 is the time required to read the X-ray image from the X-ray detector 130, typically approximately 130 ms. The scrubs 265 occur when reads of the X-ray detector 130 are triggered, but the result is not stored. The scrubs 265 minimize residual charges in the X-ray detector 130 that may cause image artifacts. The detector read trace 220 indicates the state of the X-ray detector 130, when the detector read trace 220 is high, a read occurs.

In operation, as described above, the patient 110 is placed between the X-ray emitter 120 and the X-ray detector 130 of an X-ray imaging system. The heart cycle monitor 140 then monitors the patient's heart cycle. The heart cycle monitor 140 is used to control the X-ray emitter 120 and X-ray detector 130 to synchronize X-ray acquisition with the patient's 110 cardiac cycle.

That is, first, the cardiac trigger 215 occurs as the patient's 110 heart contracts. The cardiac trigger is detected by the heart cycle monitor 140 after the delay time 230. Once the cardiac trigger has been detected, the system 100 concludes the present detector read (as shown on the detector read trace 220) and then causes the X-ray emitter 120 to emit the first kVp X-ray emission 255, for example, a high kVp X-ray emission. The X-rays emitted by the X-ray emitter 120 pass through the patient 110 and are detected by the X-ray detector 130 to form an X-ray image. After the fixed frame time 240, the X-ray detector 130 begins a read operation to read the X-ray image. The read requires the detector readout time 250. Once the read has been completed, the system 100 then causes the X-ray emitter 120 to emit the second kVp X-ray emission 255, for example, a low kVp X-ray emission. As before, the X-rays emitted by the X-ray emitter 120 pass through the patient 110 and are detected by the X-ray detector 130 to form an X-ray image. After another fixed frame time 240, the X-ray detector 130 begins a second read operation to read the X-ray image. The second read operation requires the detector readout time 250.

Once the reads for the high and low kVp X-ray emission have been concluded, the system 100 performs a number of scrubs 265. The scrubs 265 minimize residual charges in the X-ray detector 130 that may cause image artifacts. The scrubs 265 preferably continue for 1–3 seconds. Alternatively the scrubs 265 may continue to occur until the heart cycle monitor 140 detects a new cardiac trigger. Then, the system 100 reads an offset frame 270 from the X-ray detector 130. The offset frame 270 is then subtracted from the image frames read earlier to minimize system artifacts in the images. That is, the offsets are images that are acquired without any X-ray exposure (dark current). The offsets are subtracted from the X-ray images to remove artifacts such as detector structures, for example.

As mentioned above, using fixed exposure time, the time between X-rays is based on the longest exposure, which is typically the low energy exposure. The offset frame (panel read after no x-rays present) must have the same acquisition time as the two x-ray frames, and is subtracted from each of the two images. The number of scrubs (panel reads without data transfer), n, is typically on the order of 4. The scrubs prevent lag effects from occurring in the offset image. One scrub could also separate the two x-rays to reduce lag between images. However, this increases the risk of acquiring the second acquisition during the next contraction phase of the heart.

Additionally, with fixed frame time, the exposure time for the high kVp X-ray image, the exposure time for the low kVp X-ray image, and the offset all have the same interval time. Typically, the cardiac trigger could arrive at any time between scrub cycles. Acquisition of the first X-ray image may be acquired following the end of the next panel readout. Although not labeled, the highs in the detector read trace 220 prior to the high kVp X-ray emission 355 are also scrubs. The detector readout time 330 is typically constant for a given X-ray system and is based on the panel size of the X-ray system.

Figure 3:
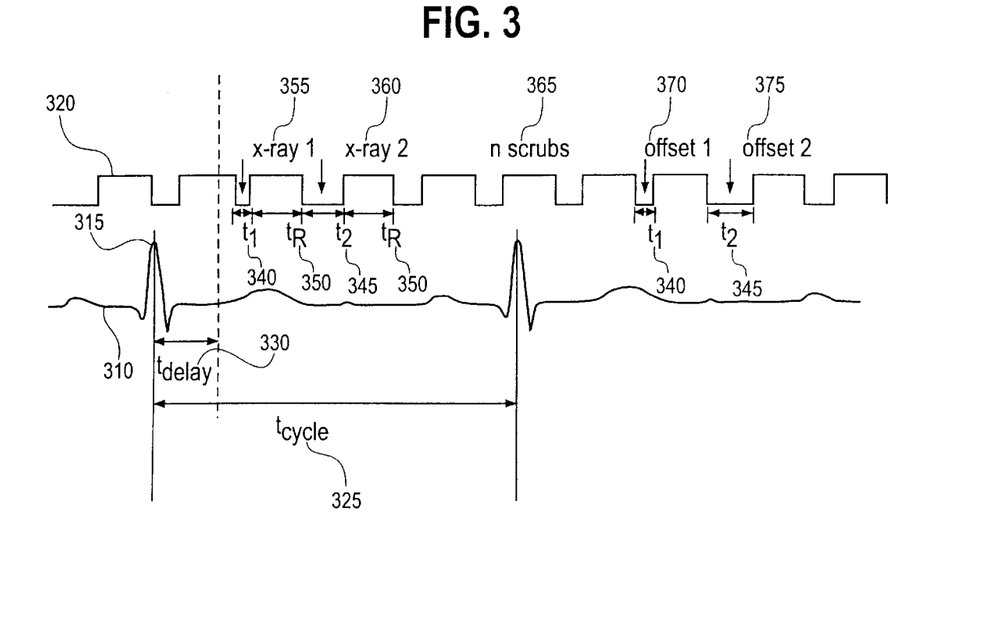
FIG. 3 illustrates the synchronization system as applied with variable frame time, acquisition on next read, and both kVp exposures in the same heart cycle according to a preferred embodiment of the present invention.

FIG. 3 illustrates the synchronization system 100 as applied with variable frame time, acquisition on next read, and both kVp exposures in the same heart cycle according to a preferred embodiment of the present invention. FIG. 3 includes a heart cycle trace 310, a cardiac trigger 315, a detector read trace 320, cycle time ($t_{cycle}$) 325, delay time ($t_{delay}$) 330, high kVp frame time ($t_1$) 340, low kVp frame time ($t_2$) 345, detector readout time ($t_R$) 350, a high kVp X-ray emission 355, a low kVp X-ray emission 360, scrubs 365, a high kVp offset 370, and a low kVp offset 375.

In operation, FIG. 3 is similar to FIG. 2 above, except the system 100 of FIG. 3 employs a variable frame time. That is, the system 100 employs a shorter delay between detector readout for the high energy image and a longer delay between detector readouts for the low energy image. As described above with respect to FIG. 2, the cardiac trigger 315 of the heart cycle trace 310 is detected by the heart cycle monitor 140 after the delay time 330. The system 100 concludes its detector read and then causes the X-ray emitter 120 to emit high kVp X-rays. After the high kVp frame time 340, the system 100 reads the X-ray image from the X-ray detector 130 during the detector readout time 350. The system 100 then causes the X-ray emitter 120 to emit low kVp X-rays. After the low kVp frame time 345, the system 100 reads the X-ray image from the X-ray detector 130 during the detector readout time 350.

Similar to FIG. 2 above, once the reads for the high and low kVp X-ray emission have been concluded, the system 100 performs a number of scrubs 265. Because the high kVp frame time 340 is different from the low kVp frame time 345, the system 100 records the high kVp offset 270 for use in processing the high kVp image and the lose kVp offset 275 for use in processing the low kVp image. Following the scrubs 265, the system 100 delays the high kVp exposure length and reads the high kVp offset frame 270 from the X-ray detector 130. Once the kVp kVp offset frame 270 has been recorded, the system 100 then records the low kVp offset frame 375 after the low kVp delay frame.

Variable frame time further reduces the time between exposures during a heart cycle, thus also reducing motion artifacts in the resultant image. The variable frame time reduces the time between exposures by taking advantage of the short exposure time of the high kVp image. Preferably, the high kVp image is acquired first.

Figure 4:
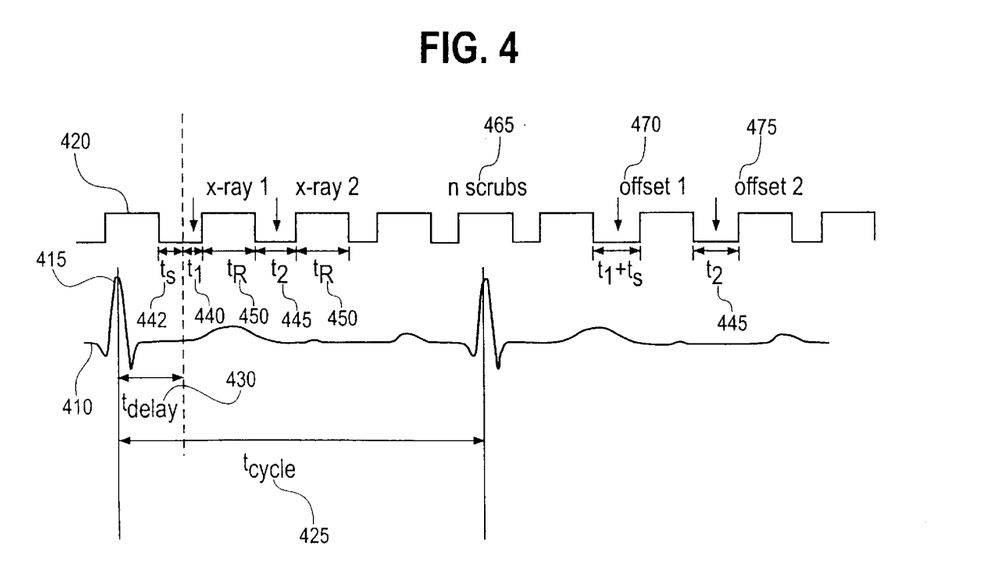
FIG. 4 illustrates the synchronization system as applied with variable frame time, immediate-preplanned image acquisition based on monitored heart rate, and both kVp exposures in the same heart cycle according to a preferred embodiment of the present invention.

FIG. 4 illustrates the synchronization system 100 as applied with variable frame time, immediate-preplanned image acquisition based on monitored heart rate, and both kVp exposures in the same heart cycle according to a preferred embodiment of the present invention. FIG. 4 includes a heart cycle trace 410, a cardiac trigger 415, a detector read trace 420, cycle time ($t_{cycle}$) 425, delay time ($t_{delay}$) 430, high kVp exposure time ($t_1$) 440, stable time 442, low kVp exposure time ($t_2$) 445, detector readout time ($t_R$) 450, scrubs 465, a high kVp offset 470, and a low kVp offset 475.

In operation, FIG. 4 is similar to FIG. 3 above, except the system 100 of FIG. 4 employs immediate, preplanned image acquisition based on a monitored heart rate acquisition of the X-ray image rather than waiting until the end of the next X-ray detector read to begin acquisition. That is, the system 100 uses the heart cycle monitor 140 to monitor the heart cycle to predict when the cardiac trigger 415 is going to occur and then schedules the X-ray transmission to occur immediately thereafter, followed by a read of the detector 130. The concept is to have the first exposure occur at the end of a "stable" time by predicting that the trigger is occurring during that time.

As described above with respect to FIG. 2, the cardiac trigger 415 of the heart cycle trace 410 is detected by the heart cycle monitor 140 after the delay time 430. The system 100 has been monitoring the heart cycle trace 410 for preferably at least the past two heart cycles and determines the probable time of occurrence of the next cardiac trigger based on the average cycle time 425 for the previous cycles. The system 100 thus ceases scrubs from the previous heart cycle so that the system 100 is not reading from the X-ray detector 130 when the next cardiac trigger 415 is detected. The stable time 422 is the time between last detector read and detection of cardiac trigger during which the system 100 remains stable and does not perform a read of the X-ray detector 130.

Once the cardiac trigger 415 is detected after the delay time 430, the system immediately transmits the high kVp X-ray exposure 455. After the high kVp exposure time 440, the system 100 reads the X-ray image from the X-ray detector 130 during the detector readout time 450. The system 100 then causes the X-ray emitter 120 to emit the low kVp X-ray exposure 460. After the low kVp exposure time 445, the system 100 reads the X-ray image from the X-ray detector 130 during the detector readout time 450. The system 100 then performs a number of scrubs 465.

Similar to FIG. 3 above, once the reads for the high and low kVp X-ray emissions have been concluded, the system 100 performs a number of scrubs 365. As mentioned above, the offset delay time preferably equals the delay time of the kVp to which it corresponds. In FIG. 4, before the high energy image was read from the X-ray detector 130, the X-ray detector 130 inter-read delay was equal to the high kVp exposure time 440 plus the stable time 422. Thus, the frame time for the high kVp offset 470 preferably equals the high kVp exposure time 440 plus stable time 422 as shown. The frame time for the low kVp offset 475 remains the same as the low kVp exposure time.

Additionally, for fast heart rates, waiting until the end of the current frame cycle could lead to acquisition of the second X-ray image during systole, or contraction of the heart. Thus, the heart rate is monitored prior to the beginning of the operator's signal to initiate the sequence. Then a detector frame rate is established and may be changed in real time so that the end of a detector read is anticipated to occur just prior to the next plethysmograph signal.

Figure 5:
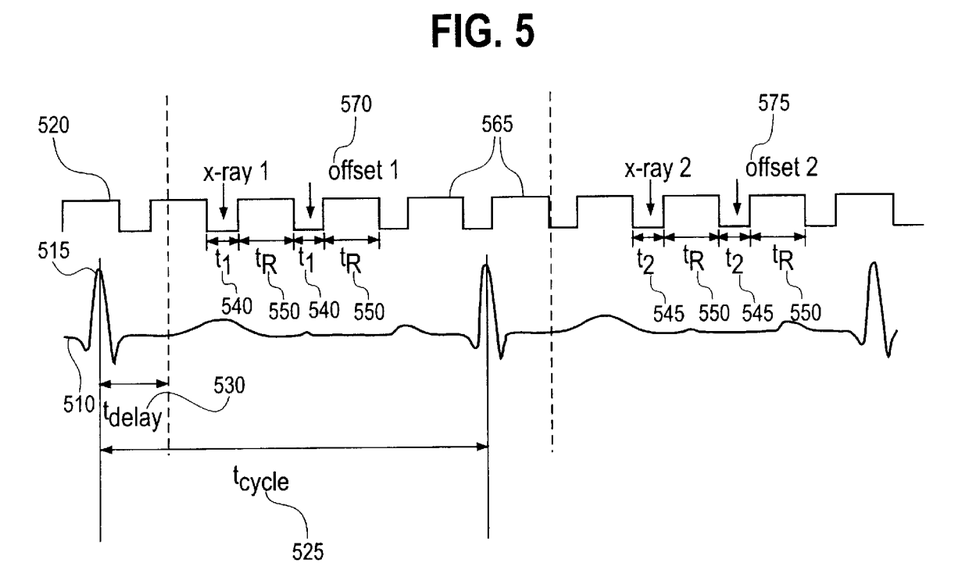
FIG. 5 illustrates the synchronization system as applied with fixed frame time, acquisition on next read, and kVp exposures in successive heart cycles according to a preferred embodiment of the present invention.

FIG. 5 illustrates the synchronization system 100 as applied with fixed frame time, acquisition on next read, and kVp exposures in successive heart cycles according to a preferred embodiment of the present invention. FIG. 5 includes a heart cycle trace 510, a cardiac trigger 515, a detector read trace 520, cycle time ($t_{cycle}$) 525, delay time ($t_{delay}$) 530, high kVp frame time ($t_1$) 540, low kVp frame time ($t_2$) 545, detector readout time ($t_R$) 550, scrubs 565, a high kVp offset 570, and a low kVp offset 575.

In operation, FIG. 5 is similar to FIG. 2 above, except the system 100 of FIG. 5 employs different kVp exposures in successive heart cycles. That is, the system 100 records the high kVp image and offset during a first cardiac cycle and then records the low kVp image and offset during a second cardiac cycle.

As described above with respect to FIG. 2, the cardiac trigger 515 of the heart cycle trace 510 is detected by the heart cycle monitor 140 after the delay time 530. Once the cardiac trigger 515 has been detected, the system 100 concludes the present detector read and then causes the X-ray emitter 120 to emit the high kVp X-ray emission 555. After the high kVp frame time 540, the system 100 reads the X-ray image from the X-ray detector 130 during the detector readout time 550. The system 100 then delays for the high kVp offset 570 and reads the detector 550. The system 100 then performs a number of scrubs 565.

Once a second cardiac trigger has been detected, the system 100 concludes the present detector read and then causes the X-ray emitter 120 to emit the low kVp X-ray emission 560. After the low kVp frame time 545, the system 100 reads the X-ray image from the X-ray detector 130 during the detector readout time 550. The system 100 then delays for the low kVp offset 575 and reads during the detector readout time 550. The system 100 then performs a number of scrubs 565.

The present invention thus minimizes potential artifacts in the heart region after subtraction of the dual energy images. The artifacts may be minimized by reducing the possibility of significant heart motion between the two images by synchronizing their acquisition to occur during portions of the heart cycle where movement is minimal. With improved image quality due to reduced motion artifacts, X-ray systems integrated with the dual energy capability may be more marketable, and may be more reliable, for example in lung cancer nodule detection in regions surrounding the heart.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for synchronizing the acquisition of images of an X-ray system with the cardiac cycle of a patient to aid in X-ray imaging of a patient, said method including the steps of:
    monitoring the patient's cardiac cycle for a first cardiac trigger;
    imaging the patient in response to said first cardiac trigger to form an X-ray image;
    monitoring the patient's cardiac cycle for a second cardiac trigger;
    recording an offset image wherein said offset image is acquired without any X-ray exposure; and
    combining the X-ray image and the offset to determine an improved X-ray image of the patient.

2. The method of claim 1 wherein said monitoring steps include monitoring the patient's cardiac cycle with a heart cycle monitor.

3. The method of claim 2 wherein said heart cycle monitor is a plethysmograph.

4. The method of claim 3 wherein said plethysmograph is a finger pulse plethysmograph.

5. The method of claim 3 wherein said plethysmograph is a wall stand integrated plethysmograph.

6. The method of claim 1 wherein said imaging step includes successively imaging the patient with high kVp X-rays and low kVp X-rays.

7. The method of claim 6 wherein said high kVp X-ray imaging is associated with a high kVp X-ray exposure time, said low kVp X-ray imaging is associated with a low kVp exposure time, and said high kVp frame time is equal to said low kVp frame time.

8. The method of claim 6 wherein said high kVp X-ray imaging is associated with a high kVp X-ray exposure time, said low kVp X-ray imaging is associated with a low kVp exposure time, and said high kVp exposure time is not equal to said low kVp exposure time.

9. The method of claim 8 wherein said high kVp exposure time is less than said low kVp exposure time.

10. The method of claim 1 wherein said step of recording an offset image includes recording an offset image using a delay time equal to the frame time for said X-ray image.

11. The method of claim 8 wherein said recording step includes recording a low kVp offset associated with the low kVp frame time and a high kVp offset associated with the high kVp frame time.

12. The method of claim 1 wherein said imaging step includes monitoring the patient's heart cycle to predict the arrival of the cardiac trigger.

13. The method of claim 12 wherein said X-ray system is controlled to allow the X-ray system to immediately image the patient upon receipt of the cardiac trigger.

14. A method for synchronizing the acquisition of images of an X-ray system with the cardiac cycle of a patient to aid in X-ray imaging of a patient, said method including the steps of:
    monitoring the patient's cardiac cycle for a first cardiac trigger;
    imaging the patient in response to said first cardiac trigger to form an X-ray image:
    monitoring the patient's cardiac cycle for a second cardiac trigger;
    recording an offset image;
    combining the X-ray image and the offset image to determine an improved X-ray image of the patient; and
    introducing at least one scrub after imaging the patient to reduce artifacts in the image.

15. A method for synchronizing the acquisition of images of an X-ray system with the cardiac cycle of a patient to aid in X-ray imaging of a patient, said method including the steps of:
    monitoring the patient's cardiac cycle for a first cardiac trigger;
    imaging the patient in response to said first cardiac trigger to form an X-ray image;
    monitoring the patient's cardiac cycle for a second cardiac trigger;
    recording an offset image:
    combining the X-ray image and the offset image to determine an improved X-ray image of the patient; and
    introducing at least one scrub between said high kVp X-ray imaging and said low kVp X-ray imaging.

16. A method for synchronizing the acquisition of images of an X-ray system with the cardiac cycle of a patient to aid in X-ray imaging of a patient, said method including the steps of:

monitoring the patient's cardiac cycle for a first cardiac trigger;

imaging the patient in response to said first cardiac trigger at a first X-ray energy to form a first X-ray image;

recording a first offset image wherein said first offset image is acquired without any X-ray exposure;

monitoring the patient's cardiac cycle for a second cardiac trigger;

imaging the patient in response to said second cardiac trigger at a second X-ray energy to form a second X-ray image;

recording a second offset image wherein said second offset image is acquired without any X-ray exposure; and combining said first X-ray image and said first offset and said second X-ray image and said second offset to determine an improved X-ray image of the patient.

17. The method of claim 16 wherein said monitoring steps include monitoring the patient's cardiac cycle with a plethysmograph.

18. The method of claim 17 wherein said plethysmograph is one of a finger pulse plethysmograph and a wall stand integrated plethysmograph.

19. The method of claim 16 wherein said first X-ray energy is associated with a first frame time, said second X-ray energy is associated with a second frame time, and said first frame time is equal to said second frame time.

20. The method of claim 16 wherein said first X-ray energy is associated with a first frame time, said second X-ray energy is associated with a second frame time, and said first frame time is not equal to said second frame time.

21. The method of claim 16 wherein said step of recording an offset image includes recording an offset image using a frame time equal to the exposure time for said X-ray image.

22. The method of claim 19 wherein said step of recording a first offset image includes recording a first offset image using a frame time equal to said first frame time and wherein said step of recording a second offset image includes recording a second offset image using an frame time equal to said second frame time.

23. The method of claim 16 wherein said imaging steps include monitoring the patient's heart cycle to predict the arrival of the cardiac trigger.

24. The method of claim 23 wherein said X-ray system is controlled to allow the X-ray system to immediately image the patient upon receipt of the cardiac trigger.

25. A method for synchronizing the acquisition of images of an X-ray system with the cardiac cycle of a patient to aid in X-ray imaging of a patient, said method including the steps of:

monitoring the patient's cardiac cycle for a first cardiac trigger;

imaging the patient in response to said first cardiac trigger at a first X-ray energy to form a first X-ray image;

recording a first offset image;

monitoring the patient's cardiac cycle for a second cardiac trigger;

imaging the patient in response to said second cardiac trigger at a second X-ray energy to form a second X-ray image;

recording a second offset image;

combining said first X-ray image and said first offset image and said second X-ray image and said second offset image to determine an improved X-ray image of the patient; and introducing at least one scrub after recording said first offset image to reduce artifacts in the image.

26. A method for synchronizing the acquisition of images of an X-ray system with the cardiac cycle of a patient to aid in X-ray imaging of a patient, said method including the steps of:

monitoring the patient's cardiac cycle for a first cardiac trigger;

imaging the patient in response to said first cardiac trigger at a first X-ray energy to form a first X-ray image;

recording a first offset image;

monitoring the patient's cardiac cycle for a second cardiac trigger:

imaging the patient in response to said second cardiac trigger at a second X-ray energy to form a second X-ray image;

recording a second offset image;

combining said first X-ray image and said first offset and said second X-ray image and said second offset to determine an improved X-ray image of the patient; and introducing at least one scrub between at least one of: said first X-ray image and said first offset; and said second X-ray image and said second offset.

27. A system for improving the image quality of a patient in an X-ray imaging system, said system including:

a heart cycle monitor for monitoring the cardiac cycle of the patient to determine a first cardiac trigger and a second cardiac trigger;

an X-ray emitter coupled to said heart cycle monitor for emitting X-rays in response to said first cardiac trigger and emitting X-rays through the patient; and an X-ray detector detecting the X-rays emitted by said X-ray emitter in response to said first cardiac trigger to form an X-ray image, acquiring an offset image without any X-ray exposure and combining said X-ray image and said offset image to form an X-ray image of the patient.

28. The system of claim 27 wherein said heart cycle monitor is a plethysmograph.

29. The system of claim 28 wherein said plethysmograph is one of a finger pulse plethysmograph and a wall stand integrated plethysmograph.

30. The system of claim 27 wherein said X-ray emitter emits X-rays in response to said first cardiac trigger at a first X-ray energy and then emits X-rays at a second X-ray energy.

31. The system of claim 30 wherein said first X-ray energy is associated with a first exposure time and said second X-ray energy is associated with second exposure time.

32. The system of claim 31 wherein said first frame time is equal to said second frame time.

33. The system of claim 31 wherein said X-ray detector reads a first offset image corresponding to said first X-ray energy and then reads a second offset image corresponding to said second X-ray energy.

34. The system of claim 31 wherein said first offset image is detected using a frame time equal to said first frame time and said second offset image is detected using a frame time equal to said second frame time.

35. The system of claim 27 wherein said heart cycle monitor monitors the patient's heart cycle to predict the arrival of the cardiac trigger.

36. The system of claim 35 wherein said X-ray emitter is controlled to immediately image the patient upon receipt of the cardiac trigger.

37. A system for improving the image quality of a patient in an X-ray imaging system, said system including:
- a heart cycle monitor for monitoring the cardiac cycle of a patient to determine a first cardiac trigger and a second cardiac trigger, wherein said heart cycle monitor monitors the patient's heart cycle to predict the arrival of the cardiac triggers;
- an X-ray emitter coupled to said heart cycle monitor for emitting X-rays in response to said first cardiac trigger and emitting X-rays through the patient;
- an X-ray detector detecting the X-rays emitted by said X-ray emitter in response to said first cardiac trigger to form an X-ray image, acquiring an offset image and combining said X-ray image and said offset image to form an X-ray image of the patient, wherein said X-ray detector introduces at least one scrub after detecting X-rays to reduce artifacts in the image.

38. A system for improving the image quality of a patient in an X-ray imaging system, said system including:
- a heart cycle monitor for monitoring the cardiac cycle of the patient to determine a first cardiac trigger and a second cardiac trigger;
- an X-ray emitter coupled to said heart cycle monitor for emitting X-rays in response to said first cardiac trigger at a first X-ray energy and emitting X-rays in response to said second cardiac trigger at a second X-ray energy; and
- an X-ray detector detecting the X-rays emitted by said X-ray emitter in response to said first cardiac trigger to form a first X-ray image, detecting a first offset image acquired without any X-ray exposure, detecting the X-rays emitted by said X-ray emitter in response to said second cardiac trigger to form a second X-ray image, detecting a second offset image acquired without any X-ray exposure, and combining said first X-ray image and said first offset image and said second X-ray image and said second offset image to form an X-ray image of the patient.

* * * * *

UNITED STATES PATENT AND TRADEMARK OFFICE
Certificate

Patent No. 6,643,536 B2                                                                      Patented: November 4, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Francois Serge Nicolas, Wauwatosa, WI; Amber Elaine Rader, Brookfield, WI; Michael John Barber, Mequon, WI; and James T. Dobbins III, Durham, NC.

Signed and Sealed this Sixth Day of September 2005.

ROBIN O. EVANS
*Supervisory Patent Examiner*
Art Unit 3742